United States Patent [19]

Ikuta et al.

[11] 4,216,292

[45] Aug. 5, 1980

[54] PROCESS FOR THE PRODUCTION OF SARCOSINE OXIDASE

[75] Inventors: Shigeru Ikuta; Kazuo Matsuura; Yoshifumi Horiuchi, all of Tagata, Japan

[73] Assignee: Toyo Jozo Kabushiki Kaisha, Tagata, Japan

[21] Appl. No.: 946,402

[22] Filed: Sep. 27, 1978

[30] Foreign Application Priority Data

Oct. 4, 1977 [JP] Japan ................................ 52-119776

[51] Int. Cl.$^2$ ............................................. C12D 13/10
[52] U.S. Cl. ..................................... 435/191; 435/17; 435/832
[58] Field of Search ................. 195/65, 66 R; 435/17, 435/191

[56] References Cited

PUBLICATIONS

Enzyme Handbook (Japan) 1966, pp. 125–126.

*Primary Examiner*—Lionel M. Shapiro
*Attorney, Agent, or Firm*—Young & Thompson

[57] ABSTRACT

An enzyme sarcosine oxidase is produced by culturing a microorganism belonging to the genus Bacillus, and particularly the species Bacillus sp. B-0618, FERM-P No. 4049, NRRL No. B-11380, and isolating the sarcosine oxidase thus produced from the culture medium. Sarcosine oxidase is useful for the determination of creatinine in the presence of creatinase and creatininase in a sample by mixing the enzymes with the sample and then measuring the generated hydrogen peroxide, formaldehyde or glycine.

2 Claims, 6 Drawing Figures

PROCESS FOR THE PRODUCTION OF SARCOSINE OXIDASE

This invention relates to a process for manufacturing sarcosine oxidase.

Sarcosine oxidase [EC. 1.5.3.1. sarcosine: oxygen oxidoreductase (demethylating) is a hitherto known enzyme which is believed to take part in the reaction:

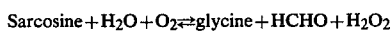
Sarcosine + $H_2O$ + $O_2 \rightleftharpoons$ glycine + HCHO + $H_2O_2$ The enzyme has been prepared from the liver or kidney of mice, or from the cultured mass of microorganisms of the genus Corynebacterium.

We have found that an enzyme, which catalyzes a reaction hereinabove illustrated, was produced in a bacterial strain B-0618, U.S. Department of Agriculture deposit NRRL No. B-11380, belonging to genus Bacillus isolated from a soil sample collected in Sasaki, Fukuchiyama, Kyoto, Japan, and have isolated a purified enzyme.

The strain B-0618 has taxonomic properties as follows:

A. Matcroscopic observation on various media, cultured at 30° C. for 18-24 hours.
(1) Bouillon agar slant:
   Growth: good, filamentous.
   Color of colony: grayish white to pale brown, almost no diffusible pigment.
(2) Glucose bouillon agar slant:
   Growth: good, filamentous.
   Color of colony: grayish white to pale brown, less diffusible pigment.
(3) Bouillon broth:
   Cultured broth: turbid and sediment, no pellicle formation.
(4) Litmus milk:
   Alkalization at about 1-2 weeks.
(5) Bouillon gelatin slab:
   Growth: grown on surface, weak but funnel-shaped liquefaction.

B. Microscopic observation:
(1) Shape and size of cells: large and straight rod, 1.0–1.5×2.0–5 μm, round edge, single or double linkage, sometimes short linkage.
(2) Polymorphism: none.
(3) Motility: peritricic locomotion (observed and bouillon agar slant medium at 26° C., 18 hours culture).
(4) Spore: cylindrical or oospherical (elliptical), at center or near edge of cell. No swelling by spore, 0.8–1.0×1.2–1.6 μm.
(5) Gram's stain: positive.
(6) Acid-fast stain: negative.

C. Physiological properties:
Nitrate reduction: negative.
Denitrification reaction: negative.
MR test: negative.
VP test: negative.
Indole formation: negative.
Hydrogen sulfate formation: positive.
Starch hydrolysis: negative.
Gelatine hydrolysis: positive.
Casein hydrolysis: negative.
Esculin hydrolysis: negative.
Cellulose hydrolysis: negative.
Citrate utilization, Simons medium: negative. Christensen medium: positive.
Nitrate utilization: positive.
Ammonium utilization: negative.
Formation of ammonium from nitrate: positive.
Growth pH: pH 6.4–9.6.
Growth temperature: 10°–42° C.
Halotolerance: NaCl 6.0%.
Behavior in oxygen: aerobic.
O-F test (Hugh Leifson medium): NT.
O-F test*: 0 (oxidative decomposition).
* O-F test medium: modified medium;

Due to no acid formation from glucose, and no or only weak formation of acid from other saccharides, glycerol was used as sugar. $NH_4H_2PO_4$ 1.0 g, KCl 0.2 g, $MgSO_4.7H_2O$ 0.2 g, yeast extract powder 1.0 g, agar powder 3.0 g, Bromthymol Blue (10% aqueous solution) 10 ml, distilled water 1000 ml, pH 7.2–7.4.

| Acid and gas formation from sugar:** (No gas formation was observed). | | | | | |
|---|---|---|---|---|---|
| L-arabinose: | — | cellobiose: | — | dulcitol: | — |
| erythritol: | — | fructose: | +(acid) | galactose: | — |
| glucose: | — | glycerol: | +(acid) | inositol: | — |
| lactose: | — | maltose: | — | mannitol: | +(acid) |
| mannose: | — | melezitose: | — | melibiose: | — |
| raffinose: | — | L-rhamnose: | — | salicin. | — |
| L-sorbose: | — | sorbitol: | — | starch: | — |
| sucrose: | — | trehalose: | — | xylose: | — |

**basal medium: $NH_4H_2PO_4$ 1.0 g, KCl 0.2 g, $MgSO_4 . 7H_2O$ 0.2 g, yeast extract powder 1.0 g, agar powder 3.0 g, Bromthymol Blue (10% aqueous solution) 10 ml, distilled water 1000 ml, pH 7.2–7.4. Sugar 10 g was added therein.

Consulting Bergey's Manual of Determinative Bacteriology, 8th Ed. 1974, the strain B-0618 having the taxonomical properties hereinabove, especially Gram positive, spore-forming large bacillus, peritricic locomotion aerobic bacteria, and acid formation from glucose, is referred to as belonging to genus Bacillus group bacteria.

Comparison of the strain B-0618 with the other bacteria that resemble it, *Bacillus badius*, *Bacillus freudenreichii* and *Bacillus macroides*, is carried out as follows.
*Bacillus badius* ATCC-14574 (type culture).
*Bacillus freudenreichii* ATCC-7053 (non-type culture, non-original strain).
*Bacillus macroides* ATCC-12905 (type culture).

| | Strain B-0618 | Bacillus badius ATCC-14574 | Bacillus freudenreichii ATCC-7053 | Bacillus macroides ATCC-12905 | Remarks |
|---|---|---|---|---|---|
| O-F test | No acid formation | | | | Hugh Leifson medium |
| O-F test | 0 | 0 | No acid formation | | O-F test medium above-described |
| catalase | + | + | + | + | |
| oxidase | + | + | + | − | |
| urease | + | − | + | − | |

-continued

| | Strain B-0618 | Bacillus badius ATCC-14574 | Bacillus freudenreichii ATCC-7053 | Bacillus macroides ATCC-12905 | Remarks |
|---|---|---|---|---|---|
| gelatin liquefaction | + | + | (+) | − | |
| starch hydrolysis | − | − | − | − | |
| esculin hydrolysis | (+) | − | − | − | |
| indole formation | − | − | − | − | |
| H$_2$S formation | + | − | − | − | |
| acetone formation | − | − | − | − | |
| MR test | − | − | − | − | |
| nitrate reduction | − | − | − | − | |
| citrate utilization | + | + | + | + | |
| Formation of acid from sugar: | | | | | |
| arabinose | − | − | − | − | |
| fructose | + | − | − | − | |
| galactose | − | − | − | − | |
| glucose | − | − | − | − | |
| glycerol | + | +* | − | − | *later alkalinization |
| inositole | − | − | − | − | |
| lactose | − | − | − | − | |
| maltose | − | − | − | − | |
| mannitol | + | − | − | − | |
| mannose | − | − | − | − | |
| sorbitol | − | − | − | − | |
| sucrose | − | − | − | − | |
| trehalose | − | − | − | − | |
| xylose | − | − | − | − | |

Characteristics in bouillon medium are as follows:
The strain B-0618: weak growth, woolly sediment.
ATCC-14574: uniformly turbid, partial sediment.
ATCC-7053: weak growth, woolly sediment.
ATCC-12905: weak growth, uniformly turbid, partial sediment.

As a result, the taxonomical properties of the strain B-0618 were different from several points of those of the compared strains as follows:

Bacillus badius ATCC-14574: formation of urease, acid formation from glycerol (acid formation and later alkalinization) and mannitol.

Bacillus freudenreichii ATCC-7053: growth on liquid culture and urease formation (slightly resemble). Esculin hydrolysis, acid formation from fructose, glycerol and mannose. ATCC-7053 strain is neither a type culture nor an original strain, and hence it cannot be identified with the strain B-0618. Thus the strain cannot belong to new species.

Hence the strain B-0618 is referred to as Bacillus sp. and designated as Bacillus sp. B-0618. This strain was deposited for permanent collection in the Institute for Microbial Industry and Technology, Agency of Industrial Science and Technology, Japan, as deposition No. FERM-P No. 4049. The strain was also deposited in ARS, U.S.A. as NRRL No. B-11380 and in Deutsche Sammlung von Mikro-Organismen, West Germany.

An object of the present invention is to provide a process for the production of enzyme sarcosine oxidase which comprises culturing a sarcosine oxidase-producing microorganism belonging to genus Bacillus in a nutrient culture medium and isolating the sarcosine oxidase from the cultured mass.

Other objects, features and advantages of the present invention will become apparent from a consideration of the following description, taken in connection with the accompanying drawings, which are graphs or diagrams illustrating the present invention, and in which more particularly:

Figure 1:
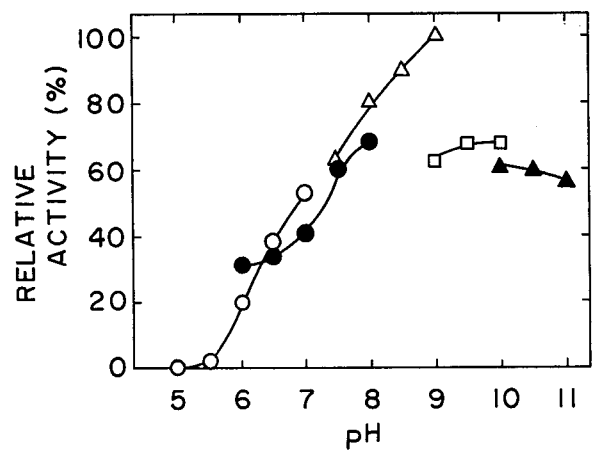
FIG. 1 is a graph of optimum pH sarcosine oxidase.

In an embodiment of the present invention, Bacillus sp. B-0618 FERM-P No. 4049 is cultured in a conventional medium for antibiotic or enzyme production. Submerged aeration culture is preferable for industrial production.

A conventional medium for microorganisms can preferably be used. For the nitrogen sources, assimilable nitrogen sources such as corn steep liquor, soybean powder, peptone, meat extracts, yeast extracts, ammonium sulfate, ammonium chloride, or the like can be used. Assimilable carbon sources such as glucose, molasses, starch hydrolyzates or the like can preferably be used. Various inorganic salts such as sodium chloride, potassium chloride, magnesium sulfate, potassium hydrogen phosphate or potassium dihydrogen phosphate are optionally used. The addition of creatine to the medium, preferably 0.5%–1%, stimulates the production of sarcosine oxidase.

The culturing temperature can be selected within the ranges for growth of microbial cells and production of an enzyme, and is preferably 26°–33° C. The culturing time can be selected depending on conditions and is usually 15–25 hours. Culturing should naturally be terminated when the sarcosine oxidase production is substantially complete.

Sarcosine oxidase exists in the cells of microorganisms.

To separate sarcosine oxidase from the cultured mass, the cultured mass is centrifuged and the wet cells are suspended in a buffer such as tris-HCl buffer, and disrupted by treatment with lysozyme, sonication or a French press. The thus-obtained crude sarcosine oxidase is purified by conventional isolation and purification methods for protein and enzyme. For example, if required after removing nucleic acid by adding protamine sulfate, fractional precipitation with acetone, methanol, ethanol or isopropanol and salting out with ammonium sulfate are preferably applied. Further purification can be achieved by for example, chromatography in which the crude sarcosine oxidase is dissolved in tris-HCl buffer and chromatographed using anion exchangers such as diethylamino ethyl-cellulose or -dextran gel, and gel filtration agents such as dextran gel or polyacrylamide gel. Purified sarcosine oxidase can be stored as a lyophilized powder.

Sarcosine oxidase produced by the present invention has the following physico-chemical properties:

(1) Enzyme action:

One mole of sarcosine consumes one mole of $H_2O$ and one mole of oxygen and generates one mole of glycine, one mole of formaldehyde and one mole of hydrogen peroxide. The enzyme catalyzes oxidation of sarcosine to form glycine and formaldehyde.

$$CH_3NHCH_2COOH + O_2 + H_2O \rightarrow H_2NCH_2COOH + HCHO + H_2O_2$$

Enzyme assay is carried out as follows:

To a reaction mixture (0.5 ml) consisting of 0.2 mole tris-HCl buffer (pH 8.0, 0.05 ml), 4-aminoantipyrine (3 mg/ml, 0.05 ml), 0.2% phenol (0.05 ml), peroxidase (0.5 mg/ml, 0.05 ml), 1 mole sarcosine (0.1 ml), and distilled water (0.2 ml) is added the enzyme solution (10 µl) and the mixture is incubated at 37° C. for 5 minutes. Ethanol (2.5 ml) is added to terminate the reaction. Formation of hydrogen peroxide is measured by colorimetric method on an absorbance at 480 nm.

A unit (1 unit, 1 u.) of enzyme activity is defined as the amount of enzyme which generates 1 µmole of hydrogen peroxide per minute.

(2) Substrate specificity:

To a reaction mixture (0.5 ml) consisting of 0.2 mole tris-HCl buffer (pH 8.0, 0.05 ml), 4-aminoantipyrine (3 mg/ml, 0.05 ml), 0.2% phenol (0.05 ml), peroxidase (0.5 mg/ml, 0.05 ml), distilled water (0.2 ml) and the following substrates (0.5 mole, 0.20 ml) is added sarcosine oxidase (0.5 unit) and the mixture is incubated at 37° C. for 5 minutes. Ethanol (2.5 ml) is added to terminate the reaction, and colorimetrically assayed at 480 nm.

Relative activity on several substrates is as follows:

| Substrate | Relative activity |
|---|---|
| Sarcosine | 100.0 |
| Choline | 0 |
| Betaine | 0.03 |
| Dimethyl glycine | 0.01 |
| Glycine | 0.06 |
| Serine | 0 |
| Threonine | 0 |
| Alanine | 0 |
| Valine | 0 |
| Lysine | 0.09 |
| N-methylethanolamine | 0 |
| N-dimethyletanolamine | 0 |

(3) Optimum pH:

In order to avoid an effect of 4-aminoantipyrine-phenol-peroxidase on chromogen, formation of aldehyde is determined by acetylacetone method. The result is shown in FIG. 1 in which optimum pH is 8.0–9.5.

Buffer solutions used are: pH 4–7: dimethylglutarate buffer, pH 6–8: phosphate buffer, pH 7.5–9: tris-HCl buffer, pH 9–10: glycine - NaOH buffer and pH 10–11: sodium carbonate - borate buffer.

Figure 2:
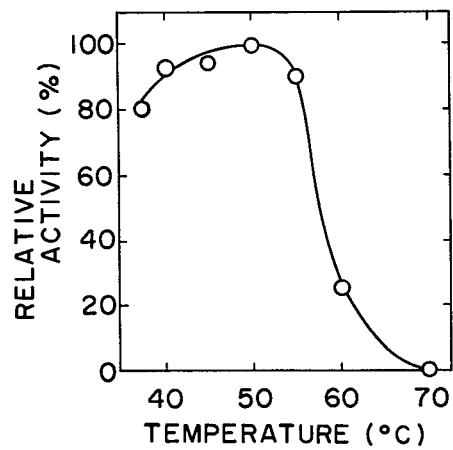
FIG. 2 is a graph of relative activity versus temperature for sarcosine oxidase.

(4) Optimum temperature:

Around 50° C. as shown in FIG. 2. Substrate: sarcosine.

Figure 3:
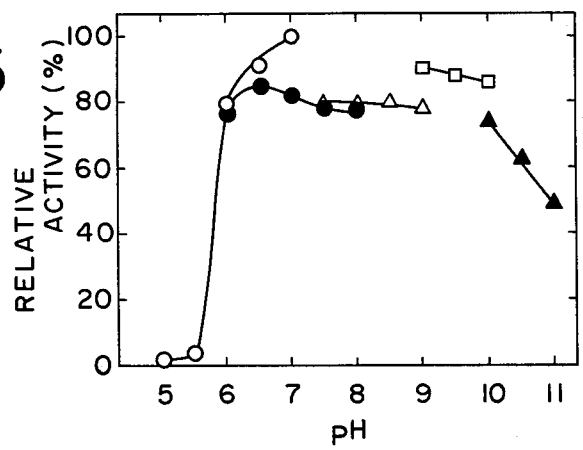
FIG. 3 is a graph of pH-stability for sarcosine oxidase.

(5) pH-stability:

Dimethylglutarate buffer for pH 5–7, phosphate buffer for pH 6–8, tris-HCl buffer for pH 7.5–9, glycine-NaOH buffer for pH 9–10 and sodium carbonate-borate buffer for pH 10–11 are used. To 0.1 ml of each buffer, 100 µl enzyme solution (protein 100 µg/, ml) was added and allowed to stand for 60 minutes at 37° C. After pH is adjusted by adding 1.0 mole tris-HCl buffer (pH 8.0, 0.3 ml) thereto and 20 µl of sample is taken therefrom, enzyme activity is determined. Sarcosine is used as the substrate and as shown in FIG. 3, the stable pH is about pH 6.0–10.0.

Figure 4:
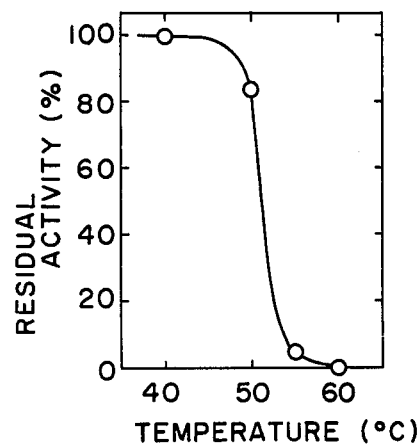
FIG. 4 is a graph of heat stability of sarcosine oxidase.

(6) Heat stability:

Heat stability of the enzyme is determined by incubating 10 m mole tris-HCl buffer (0.5 ml, pH 8.0) containing enzyme (protein 20 µg/ml) at various temperatures for 10 minutes using sarcosine as a substrate. As shown in FIG. 4 the enzyme is stable below about 40° C.

(7) Molecular weight:

40,000 (measured by gel filtration method).

(8) Isoelectric point:

4.7 (electrophoresis using carrier-type ampholyte).

(9) Identification and determination of reaction products:

(i) Identification of glycine:

| Reaction mixture: | | |
|---|---|---|
| 0.2 mole tris-HCl buffer (pH 8.0) | 1.0 | ml |
| 1 m mole sarcosine | 1.0 | ml |
| catalase | 200 | u. |
| sarcosine oxidase | 5 | u. |
| distilled water | 8.0 | ml |
| total | 10.0 | ml |

The above reaction mixture (10 ml) was incubated at 37° C. for 60 minutes after which the reaction was terminated by heating at 100° C. for 5 minutes. Precipitate formed was removed by centrifugation and the supernatant was concentrated up to ten times which was spotted on a filter paper. A chromatogram was developed with water-saturated phenol overnight and colored by heating after spraying with ninhydrin solution. Rf value was observed as 0.26.

Known samples of sarcosine and glycine were shown as having Rf values of 0.66 and 0.26 respectively, whereby a spot showing the above Rf value was identified as glycine.

(ii) Determination of formaldehyde:

| Reaction mixture: | | |
|---|---|---|
| 0.2 mole tris-HCl buffer (pH 8.0) | 0.05 | ml |
| sarcosine of aliquot concentration | 0.10 | ml |
| catalase | 200 | u. |
| sarcosine oxidase | 3.0 | u. |
| distilled water | 0.35 | ml |
| total | 0.50 | ml. |

Figure 5:
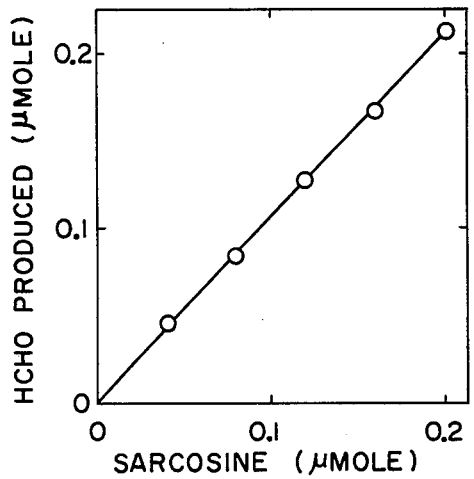
FIG. 5 is a graph showing the result of quantitative analysis or sarcosine by determination of formaldehyde.

The reaction mixture was incubated at 37° C. for 20 minutes. Reaction was terminated by heating for 5 minutes and after cooling acetate buffer (pH 5.5, 1;5 ml) was added thereto, further the chromogen solution hereinbelow (20 ml) was added. After 50 minutes incubation at 37° C., the solution was colorimetrically measured at 412 nm. The results are shown in FIG. 5, in which formation of formaldehyde corresponds to concentration of sarcosine.

| Chromogen: | | |
|---|---|---|
| ammonium acetate | 15 | g |
| acetic acid | 0.3 | ml |
| acetylacetone | 0.2 | ml |
| water to 100 ml | | |

(iii) Determination of hydrogen peroxide:

Hydrogen peroxide was quantitatively determined by conjoint 4-aminoantipyrine-phenol-peroxidase.

| Reaction mixture: | | |
|---|---|---|
| 0.2 mole tris-HCl buffer solution (pH 8.0) | 0.05 | ml |
| 3 mg/ml 4-aminoantipyrine | 0.05 | ml |
| 0.2% phenol | 0.05 | ml |
| 0.5 mg/ml peroxidase | 0.05 | ml |
| sarcosine of aliquot concentration | 0.10 | ml |
| sarcosine oxidase | 3.0 | u. |
| distilled water | 0.2 | ml |
| total | 0.5 | ml. |

Figure 6:
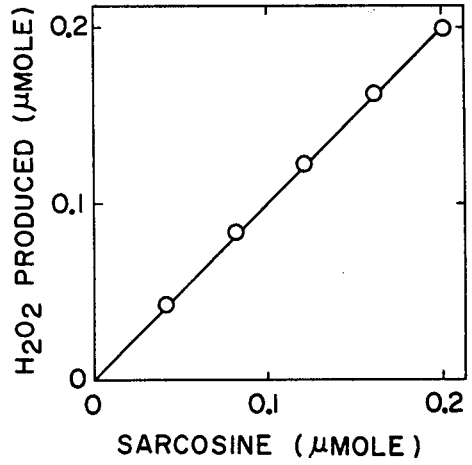
FIG. 6 is a graph showing the result of quantitative analysis of sarcosine by determination of hydrogen peroxide.

The reaction mixture was incubated at 37° C. for 20 minutes. After adding ethanol (2.5 ml) the mixture was colorimetrically measured at 480 nm. As shown in FIG. 6 formation of hydrogen peroxide correspond to the concentration of sarcosine.

As hereinabove explained, the enzyme sarcosine oxidase of the present invention catalyzes the oxidation reaction wherein sarcosine is reacted with oxygen (in which one mole of water is consumed for one mole of sarcosine) and glycine, formaldehyde and hydrogen peroxide are formed. Therefore the enzyme is confirmed as the enzyme of EC. 1.5.3.1 sarcosine: oxygen oxidoreductase (demethylating).

The sarcosine oxidase can be used as an enzymatic diagnostic reagent as in assaying for creatinine in blood or urine with the combination of creatinase and creatininase. Further, sarcosine oxidase can be used for assaying the activity of creatininase.

The following example illustrates an embodiment of the present invention but is not to construed as limiting the invention.

EXAMPLE

A medium (100 ml) comprising creatine (0.5%), fish solubles (0.5%), yeast extract (0.2%), KCl (0.3%), $K_2HPO_4$ (0.1%) and $MgSO_4.7H_2O$ (0.05%) in a 500 ml Erlenmeyer flask was sterilized at 120° C. for 20 minutes. Bacillus sp. B-0618 FERM-P No. 4049 inoculated therein was cultured at 30° C. for one day as a seed culture, which was transferred to the same sterilized medium (20 l) in a 30-liter jar fermenter and cultured at 30° C. for 20 hours, at 200 r.p.m., aeration 20 l/min. Bacterial cells centrifugally collected (12 g) were washed with 10 m mole phosphate buffer (pH 7.0), suspended in the same buffer solution, and lysozyme (final concentration 0.2 mg/ml) was added and stirred at 37° C. for 30 minutes. The supernatant obatined centrifugally at 5000 r.p.m. for 15 minutes was collected (sarcosine oxidase activity: 1400 u.). To the thus-obtained supernatant was added 2% protamine sulfate solution (2.5 ml) and the nucleic acid precipitate was separated.

To the supernatant was added saturated ammonium sulfate and the precipitate of fractions of 50%–70% ammonium sulfate concentration was collected. The precipitate was dissolved in 10 mM tris-HCl buffer (pH 8.0, 20 ml) and desalted through a Sephadex G-25 column (3.5×30 cm). The desalted solution was subjected to a DEAE-cellulose column (2.0×18 cm, buffered with 10 mM tris-HCl buffer, pH 7.0) to absorb the enzyme, washed with the same buffer solution containing 0.1 mole KCl, and eluted by the gradient of 0.1 M–0.5 M KCl solutions.

The active fraction which was eluted at 0.36 M KCl was collected and dialyzed for 10 hours against the solution of 10 mM tris-HC1 buffer (pH 8.0), then freeze dried to obtain a powder of sarcosine oxidase.

Total activity: 540 units, protein: 43 mg, specific activity: 12.7 u./mg, recovery 38.6%.

We claim:

1. A process for the production of sarcosine oxidase which comprises culturing a sarcosine-oxidase-producing microorganism Bacillus sp. B-0618, FERM-P No. 4049, NRRL No. B-11380, in a nutrient culture medium and isolating the sarcosine oxidase thus produced from the cultured mass thereof.

2. A process as claimed in claim 1 wherein the culture medium contains creatine.

* * * * *